US009663448B2

(12) United States Patent
Priel et al.

(10) Patent No.: US 9,663,448 B2
(45) Date of Patent: *May 30, 2017

(54) TRI-ARYL COMPOUNDS AND COMPOSITIONS COMPRISING THE SAME

(71) Applicant: BEN-GURION UNIVERSITY OF THE NEGEV RESEARCH AND DEVELOPMENT AUTHORITY, Beer Sheva (IL)

(72) Inventors: Esther Priel, Beer Sheva (IL); Aviv Gazit, Jerusalem (IL); Shimon Slavin, Jerusalem (IL); Sara Yitzchak, Tiberias (IL)

(73) Assignee: BEN-GURION UNIVERSITY OF THE NEGEV RESEARCH AND DEVELOPMENT AUTHORITY, Beer Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/070,073

(22) Filed: Nov. 1, 2013

(65) Prior Publication Data

US 2014/0107336 A1  Apr. 17, 2014

Related U.S. Application Data

(63) Continuation of application No. 12/602,632, filed as application No. PCT/IL2008/000747 on Jun. 3, 2008, now Pat. No. 8,604,245.

(60) Provisional application No. 60/924,875, filed on Jun. 4, 2007, provisional application No. 60/929,524, filed on Jul. 2, 2007, provisional application No. 60/929,525, filed on Jul. 2, 2007, provisional application No. 61/006,924, filed on Feb. 6, 2008.

(51) Int. Cl.
| | |
|---|---|
| *C07C 215/80* | (2006.01) |
| *A61K 31/03* | (2006.01) |
| *A61K 31/05* | (2006.01) |
| *A61K 31/055* | (2006.01) |
| *A61K 31/136* | (2006.01) |
| *A61K 31/66* | (2006.01) |
| *A61K 31/695* | (2006.01) |
| *C07C 215/50* | (2006.01) |
| *C07D 213/16* | (2006.01) |
| *C07D 213/30* | (2006.01) |
| *C07D 295/096* | (2006.01) |
| *C07C 43/225* | (2006.01) |
| *C07D 295/135* | (2006.01) |
| *C07C 39/367* | (2006.01) |
| *C07C 43/23* | (2006.01) |
| *C07F 9/50* | (2006.01) |

(52) U.S. Cl.
CPC ............ *C07C 215/80* (2013.01); *A61K 31/03* (2013.01); *A61K 31/05* (2013.01); *A61K 31/055* (2013.01); *A61K 31/136* (2013.01); *A61K 31/66* (2013.01); *A61K 31/695* (2013.01); *C07C 39/367* (2013.01); *C07C 43/225* (2013.01); *C07C 43/23* (2013.01); *C07C 215/50* (2013.01); *C07D 213/16* (2013.01); *C07D 213/30* (2013.01); *C07D 295/096* (2013.01); *C07D 295/135* (2013.01); *C07F 9/5022* (2013.01)

(58) Field of Classification Search
None
See application file for complete search history.

(56) References Cited

U.S. PATENT DOCUMENTS

| | | | |
|---|---|---|---|
| 4,093,557 A | 6/1978 | Zecher | |
| 4,740,330 A * | 4/1988 | Wang | ............ C07C 41/16 552/115 |
| 4,783,495 A | 11/1988 | Pastor et al. | |
| 4,835,202 A | 5/1989 | Pastor et al. | |
| 5,198,531 A | 3/1993 | Webber | |
| 5,243,018 A * | 9/1993 | Kuze et al. | ............... 528/198 |
| 5,290,658 A | 3/1994 | Uenishi et al. | |
| 5,399,363 A | 3/1995 | Liversidge et al. | |
| 5,543,158 A | 8/1996 | Gref et al. | |
| 5,571,825 A | 11/1996 | Boschelli et al. | |
| 5,583,016 A | 12/1996 | Villeponteau et al. | |
| 5,625,027 A | 4/1997 | Kuze et al. | |
| 5,641,515 A | 6/1997 | Ramtoola | |
| 6,028,103 A | 2/2000 | Brugnara et al. | |
| 6,191,165 B1 | 2/2001 | Ognyanov et al. | |
| 6,331,564 B1 | 12/2001 | Brugnara et al. | |
| 6,380,378 B1 | 4/2002 | Kitamura et al. | |
| 6,399,738 B1 | 6/2002 | Ito | |
| 7,115,619 B2 | 10/2006 | Stevens et al. | |
| 7,846,904 B2 | 12/2010 | Harley et al. | |
| 8,604,245 B2 | 12/2013 | Priel et al. | |
| 8,609,736 B2 | 12/2013 | Gazit et al. | |
| 2002/0160939 A1 | 10/2002 | Michaeli | |
| 2004/0220186 A1 | 11/2004 | Bell et al. | |
| 2005/0049208 A1 | 3/2005 | Kaufmann et al. | |
| 2006/0111365 A1 | 5/2006 | Tauchi | |
| 2007/0042962 A1 | 2/2007 | Adams et al. | |
| 2010/0267667 A1 | 10/2010 | Gazit et al. | |

FOREIGN PATENT DOCUMENTS

| | | |
|---|---|---|
| EP | 0193256 A1 | 9/1986 |
| EP | 0397831 B1 | 9/1993 |

(Continued)

OTHER PUBLICATIONS

Lomakin, S,M, and Zaikov, G.E. "Modern Polymer Flame Retardency" 2003, Brill: Zeist, p. 71.*

(Continued)

*Primary Examiner* — David K O'Dell
(74) *Attorney, Agent, or Firm* — Lucas & Mercanti, LLP

(57) ABSTRACT

The present invention relates to a novel class of tri-aryl compounds, compositions comprising the same and processes for the preparation thereof.

4 Claims, No Drawings

(56) References Cited

FOREIGN PATENT DOCUMENTS

| EP | 0576357 | A1 | | 12/1993 |
| EP | 0604983 | A1 | | 7/1994 |
| EP | 0745600 | A1 | | 12/1996 |
| EP | 0658161 | B1 | | 7/1999 |
| EP | 1219609 | A1 | | 7/2002 |
| EP | 1112251 | B1 | | 5/2003 |
| EP | 1144395 | B1 | | 4/2005 |
| EP | 1183020 | B1 | | 8/2006 |
| EP | 2152663 | B1 | | 3/2014 |
| JP | 02121941 | A | * | 5/1990 |
| JP | 10153884 | A | * | 6/1998 ............ G03G 9/097 |
| JP | 10273461 | A | | 10/1998 |
| JP | 2001312055 | A1 | | 11/2001 |
| JP | 2005-008626 | | | 1/2005 |
| JP | 2005008626 | A | | 1/2005 |
| JP | 2006059694 | A | | 3/2006 |
| JP | 2007-016214 | | | 1/2007 |
| JP | 2007016214 | A | | 1/2007 |
| WO | 9315063 | A1 | | 8/1993 |
| WO | 9615784 | A2 | | 5/1996 |
| WO | 9731907 | A1 | | 9/1997 |
| WO | 9734589 | A1 | | 9/1997 |
| WO | 9734599 | A2 | | 9/1997 |
| WO | 9808871 | A1 | | 3/1998 |
| WO | 9835033 | A1 | | 9/1998 |
| WO | 9842691 | A1 | | 10/1998 |
| WO | 9961431 | A1 | | 12/1999 |
| WO | 0001495 | A1 | | 1/2000 |
| WO | 0018749 | A1 | | 4/2000 |
| WO | 0027848 | A2 | | 5/2000 |
| WO | 0034241 | A1 | | 6/2000 |
| WO | 0046209 | A1 | | 8/2000 |
| WO | 0104156 | A1 | | 1/2001 |
| WO | 0108677 | A1 | | 2/2001 |
| WO | 0121602 | A1 | | 3/2001 |
| WO | 0130771 | A1 | | 5/2001 |
| WO | 0140169 | A1 | | 6/2001 |
| WO | 0147935 | A2 | | 7/2001 |
| WO | 0149663 | A2 | | 7/2001 |
| WO | 0168603 | A2 | | 9/2001 |
| WO | 0213798 | A2 | | 2/2002 |
| WO | 02056880 | A1 | | 7/2002 |
| WO | 02059098 | A1 | | 8/2002 |
| WO | 02060422 | A2 | | 8/2002 |
| WO | 02100813 | A2 | | 12/2002 |
| WO | 03002531 | A2 | | 1/2003 |
| WO | 03004498 | A1 | | 1/2003 |
| WO | 03037432 | A1 | | 5/2003 |
| WO | 03059934 | A2 | | 7/2003 |
| WO | 03077949 | A2 | | 9/2003 |
| WO | 2006007864 | A1 | | 7/2004 |
| WO | 2004082667 | A1 | | 9/2004 |
| WO | 2005003129 | A1 | | 1/2005 |
| WO | 2005012485 | A2 | | 2/2005 |
| WO | 2005095381 | A1 | | 10/2005 |
| WO | 2005120514 | A1 | | 12/2005 |
| WO | 2006083869 | A2 | | 8/2006 |
| WO | 2006084031 | A1 | | 8/2006 |
| WO | 2008149346 | A2 | | 12/2008 |

OTHER PUBLICATIONS

O'Krongly "Efficient triple coupling reaction to produce a self-adjusting molecular cage." Journal of the American Chemical Society, 1985, 107(19), 5544-5.*
Bacon and Gardner, "The Reactivity of Para-Fluorine in Triarylmethyl Chlorides" J. Org. Chem., 1938, 8, 283.*
Gerald Dyker et al: "Sterically Stabilized p-Quinodimethanes by Nucleophilic Aromatic Substitution", European Journal of Organic Chemistry, vol. 2006, No. 9, May 1, 2006 (May 1, 2006), pp. 2134-2144, XP55008002, ISSN: 1434-193X, DOI: 10.1002/ejoc.200600002.
Neamati et al: "Depsides and depsidones as inhibitors of HIV-1 integrase", Journal of Medicinal Chemistry, American Chemical Society, US, vol. 40, No. 6, Mar. 14, 1997 (Mar. 14, 1997), pp. 942-951, XP002113505, ISSN: 0022-2623, DOI: 10.1021/JM960759E.
Dessalew Nigus et al: "Investigation of potential glycogen synthase kinase 3 inhibitors using pharmacophore mapping and virtual screening", Chemical Biology & Drug Design, Blackwell Publishing TD., Oxford, GB, vol. 68, No. 3, Jan. 1, 2006 (Jan. 1, 2006), pp. 154-165, XP009080602, ISSN: 1747-0277, DOI: 10.1111/J.1747-0285.2006.00430.X.
Pastor et al: "Organophosphorous and organosilicon derivatives of sterically hindered phenols", Journal of Organometallic Chemistry, Elsevier-Sequoia S.A. Lausanne, CH, vol. 376, No. 1, Oct. 24, 1989 (Oct. 24, 1989), pp. 21-29, XP022311497, ISSN: 0022-328X, DOI:10.1016/0022-328X(89)88070-2.
B. Kirste et al: "Hydrogen-1 and carbon-13 ENDOR investigations of sterically hindered galvinoxyl radicals", Journal of the American Chemical Society, vol. 103, No. 21, Oct. 1, 1981 (Oct. 1, 1981), pp. 6280-6286, XP55008118, ISSN: 0002-7863, DOI: 10.1021/ja00411a002.
Wacks M E et al: "Multiply charged ions", Recent Topics in Mass Spectrometry: Articles . . . From a NATO Study Institute of Mass Spectrometry, Gordon and Breach, US, Jan. 1, 1971 (Jan. 1, 1971), pp. 1-9, XP008143463, ISBN: 0-677-14800-3.
International Search Report issued in PCT Application No. PCT/IL2008/000747, Nov. 10, 2008.
Extended European Search Report issued in European Application No. 08763505.8, Oct. 10, 2011.
Matthew L. Peterson et al, "Expanding the Scope of Crystal Form Evaluation in Pharmaceutical Science" Journal of Pharmacy & Pharmaceutical Science 2006 (9(3) pp. 317-326.
Anthony R. West, "Solid State Chemistry and its Applications", Wiley, New York, 1988, pp. 358 & 365.
Russian Office Action for Russian Patent Application No. 201401193/28, dated Jan. 15, 2016, and English translation thereof.
Canadian Examination Report for Canadian Patent Application No. 2,690,004, dated Feb. 8, 2016.
Stephen D. Pastor et al. "Organophosphorus and organosilicon derivatives of sterically hindered phenols" Journal of Organometallic Chemistry, 376 (1989) 21-29.
Gerald Dyker et al. "Sterically Stabilized p-Quinodimethanes by Nucleophilic Aromatic Substitution" Eur. J. Org. Chem. 2006, 2134-2144.
Tichon et al., "Oxidative Stress Protection by Novel Telomerase Activators in Messenchymal Stem cells derived from Healthy and Diseased Individuals", Current Molecular Medicine 2013, 13, 1010-1022; 2013 Bentham Science Publishers, 13 pages.
Bemardes de Jesus, et al, "The telomerase activator TA-65 elongates short telomeres and increases healtj span of adult/old mice without increasing cancer incidence", Aging Cell Jul. 22, 2016; pp. 604-621, 18 pages.
International Search Report for International Application No. PCT/IL2014/050959 (Feb. 23, 2015) (2 pages).
Eurasian Office Action dated Jan. 15, 2016, which is issued for related Eurasian Application No. 201401193/28 and its English translation (5 pages).
Chan et al., "Clotrimazole and efaroxan stimulate insulin secretion by different mechanisms in rat pancreatic islets", Naunyn-Schmiedeberg's Arch Pharmacol, 1997, vol. 356, pp. 763-768.
Peterson et al., "Expanding the Scope of Crystal Form Evaluation in Pharmaceutical Science", J Pharm Pharmaceut Sci, 2006, vol. 9, No. 3, pp. 317-326.
Morissette et al., High-throughput crystallization: polymorphs, salts, co-crystals and solvates of pharmaceutical solids, Advanced Drug Delivery Reviews, 2004, vol. 56 , pp. 275-300.
Rouhi, "The Right Stuff From research and development to the clinic getting drug crystals right is full of pitfalls." Chem. & Eng. News, 2003, vol. 81, No. 8, 13 pages.
"Diabetes Document" Johns Hopkins Medical Institutions, 2001, 5 pages.

* cited by examiner

TRI-ARYL COMPOUNDS AND COMPOSITIONS COMPRISING THE SAME

CROSS-REFERENCE TO RELATED APPLICATIONS

This application is a continuation of U.S. patent application Ser. No. 12/602,632, filed Dec. 1, 2009, which is a 371 of PCT/IL2008/000747 filed Jun. 3, 2008, which claims the benefit of U.S. Provisional Patent Application Ser. Nos. 60/924,875 filed Jun. 4, 2007, 60/929,524 filed Jul. 2, 2007, 60/929,525 filed Jul. 2, 2007 and 61/006,924 filed Feb. 6, 2008, the contents of each of which are incorporated herein by reference.

FIELD OF THE INVENTION

The present invention relates to a novel class of tri-aryl compounds, pharmaceutical compositions comprising the same and methods of preparation thereof.

BACKGROUND OF THE INVENTION

Nucleic acid polymerases are enzymes, whose primary function is to polymerize new nucleic acids such as deoxyribonucleic acid (DNA) or ribonucleic acid (RNA) using an existing DNA or RNA template. Polymerases typically are involved in the processes of replication and transcription.

The primary sequences of nucleic acids are crucial for understanding the function and control of genes and for applying many of the basic techniques of molecular biology. The ability to do rapid and reliable DNA sequencing is, therefore, a very important technology. The DNA sequence is an important tool in genomic analysis as well as other applications, such as genetic identification, forensic analysis, genetic counseling, medical diagnostics, etc. With respect to the area of medical diagnostic sequencing, disorders, susceptibilities to disorders, and prognoses of disease conditions, can be correlated with the presence of particular DNA sequences or the degree of variation (or mutation) in DNA sequences, at one or more genetic loci.

Polymerases are thus useful in genetic engineering, nucleotide sequencing, DNA labeling, site-directed mutagenesis, and the like. Thermostable DNA polymerases have found application in polymerase chain reactions (PCR), and various DNA polymerases suitable for the PCR method have been developed and commercialized.

Polymerase activity can be modulated, in part, by other molecules which bind to the polymerase. Such modulation may comprise enhancing polymerase activity or diminishing such activity, which in turn modulates multiple cellular processes, and other applications. Compounds which bind to polymerases and thereby modulate its activity thus will have a wide array of important applications.

SUMMARY OF THE INVENTION

In one embodiment, this invention provides a compound represented by the structure represented by formula I:

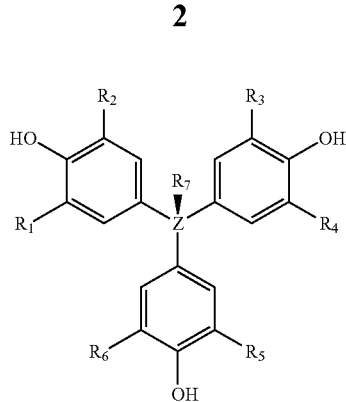

wherein
Z is carbon, nitrogen, phosphor, arsenic, silicon or germanium;
$R_1$, $R_2$, $R_3$, $R_4$, $R_5$ and $R_6$ are independently the same or different comprising alkyl ($C_2$-$C_6$), alkenyl ($C_2$-$C_6$), alkynyl ($C_2$-$C_6$), alkoxy ($C_2$-$C_6$), alkylalkoxy, haloalkyl, alkylhaloalkyl, aryl, alkylaryl, haloaryl, cycloalkyl, heterocycloalkyl, alkylcycloalkyl, alkylheterocycloalkyl, heteroaryl, alkylheteroaryl, amino, monoalkylamino, dialkylamino or arylamino; and
$R_7$ is nothing, oxo, hydrogen, hydroxy, halogen, CN, $NO_2$, alkyl ($C_1$-$C_6$), alkenyl ($C_1$-$C_6$), alkynyl ($C_1$-$C_6$), alkoxy ($C_1$-$C_6$), haloalkyl, aryl, alkylaryl, haloaryl, heterocycloalkyl, alkylheterocycloalkyl, heteroaryl or alkylheteroaryl; or its isomer, salt, hydrate, N-oxide, crystal or any combination thereof.

In one embodiment, this invention provides a compound represented by the structure represented by formula II:

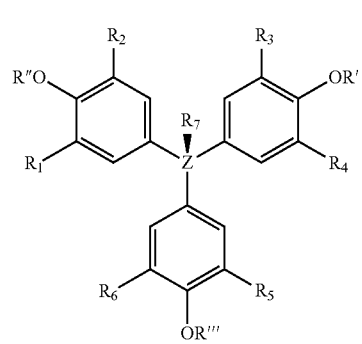

wherein
Z is carbon, nitrogen, phosphor, arsenic, silicon or germanium;
R', R" and R'" are independently the same or different comprising hydrogen, alkyl, haloalkyl, alkylamino, alkylester, phenyl, benzyl, alkanyloyl, acetyl or benzoyl;
$R_1$, $R_2$, $R_3$, $R_4$, $R_5$ and $R_6$ are independently the same or different comprising alkyl ($C_2$-$C_6$), alkenyl ($C_2$-$C_6$), alkynyl ($C_2$-$C_6$), alkoxy ($C_2$-$C_6$), alkylalkoxy, haloalkyl, alkylhaloalkyl, aryl, alkylaryl, haloaryl, cycloalkyl, heterocycloalkyl, alkylcycloalkyl, alkylheterocycloalkyl, heteroaryl, alkylheteroaryl, amino, monoalkylamino, dialkylamino or arylamino; and
$R_7$ is nothing, oxo, hydrogen, hydroxy, halogen, CN, $NO_2$, alkyl ($C_1$-$C_6$), alkenyl ($C_1$-$C_6$), alkynyl ($C_1$-$C_6$), alkoxy ($C_1$-$C_6$), haloalkyl, aryl, alkylaryl, haloaryl, heterocycloalkyl, alkylheterocycloalkyl, heteroaryl or alkylheteroaryl; or its isomer, salt, hydrate, N-oxide, crystal or any combination thereof.

In one embodiment, this invention provides a compound represented by the structure of Formula XIII:

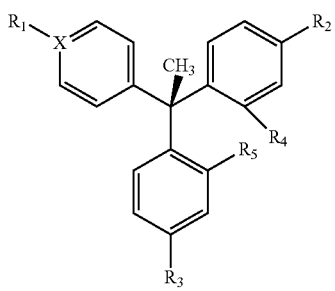

XIII wherein

X is carbon or nitrogen;

$R_1$ is nothing, alkoxy, $OCH_2COOEt$ or halogen $R_2$ and $R_3$ are independently hydrogen, alkyl, alkoxy, hydroxyl, or $OCH_2COOAlk$; and $R_4$ and $R_5$ are hydrogens or form together a saturated or unsaturated of 5-7 carbocyclic ring; or its isomer, salt, hydrate, N-oxide, crystal or any combination thereof; and a carrier, diluents, or any combination thereof In one embodiment, this invention provides a pharmaceutical composition comprising a compound of formula I:

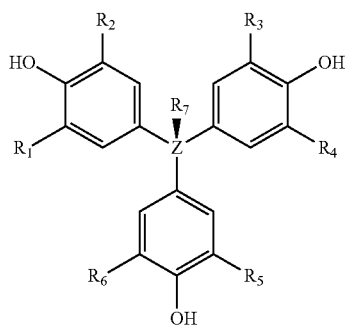

I wherein

Z is carbon, nitrogen, phosphor, arsenic, silicon or germanium;

$R_1$, $R_2$, $R_3$, $R_4$, $R_5$ and $R_6$ are independently the same or different comprising alkyl ($C_2$-$C_6$), alkenyl ($C_2$-$C_6$), alkynyl ($C_2$-$C_6$), alkoxy ($C_2$-$C_6$), alkylalkoxy, haloalkyl, alkylhaloalkyl, aryl, alkylaryl, haloaryl, cycloalkyl, heterocloalkyl, alkylcycloalkyl, alkylheterocycloalkyl, heteroaryl, alkylheteroaryl, amino, monoalkylamino, dialkylamino or arylamino; and $R_7$ is nothing, oxo, hydrogen, hydroxy, halogen, CN, $NO_2$, alkyl ($C_1$-$C_6$), alkenyl ($C_1$-$C_6$), alkynyl ($C_1$-$C_6$), alkoxy ($C_1$-$C_6$), haloalkyl, aryl, alkylaryl, haloaryl, heterocycloalkyl, alkylheterocycloalkyl, heteroaryl or alkylheteroaryl; or its isomer, salt, hydrate, N-oxide, crystal or any combination thereof; and a carrier, diluents, or any combination thereof.

In one embodiment, this invention provides a pharmaceutical composition comprising a compound of formula II:

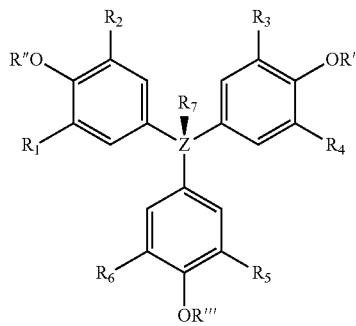

II wherein

Z is carbon, nitrogen, phosphor, arsenic, silicon or germanium;

R', R" and R'" are independently the same or different comprising hydrogen, alkyl, haloalkyl, alkylamino, alkylester, phenyl, benzyl, alkanyloyl, acetyl or benzoyl;

$R_1$, $R_2$, $R_3$, $R_4$, $R_5$ and $R_6$ are independently the same or different comprising alkyl ($C_2$-$C_6$), alkenyl ($C_2$-$C_6$), alkynyl ($C_2$-$C_6$), alkoxy ($C_2$-$C_6$), alkylalkoxy, haloalkyl, alkylhaloalkyl, aryl, alkylaryl, haloaryl, cycloalkyl, heterocycloalkyl, alkylcycloalkyl, alkylheterocycloalkyl, alkylheteroaryl, amino, monoalkylamino, dialkylamino or arylamino; and $R_7$ is nothing, oxo, hydrogen, hydroxy, halogen, CN, $NO_2$, alkyl ($C_1$-$C_6$), alkenyl ($C_1$-$C_6$), alkynyl ($C_1$-$C_6$), alkoxy ($C_2$-$C_6$), haloalkyl, aryl, alkylaryl, haloaryl, heterocycloalkyl, alkylheterocycloalkyl, heteroaryl or alkylheteroaryl; or its isomer, salt, hydrate, N-oxide, crystal or any combination thereof; and a carrier, diluents, or any combination thereof In one embodiment, this invention provides a pharmaceutical composition comprising a compound of formula XIII:

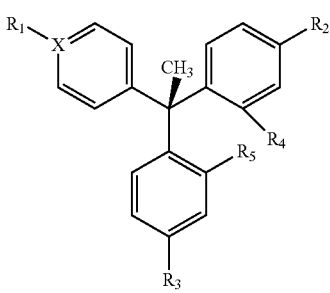

XIII wherein

X is carbon or nitrogen;

$R_1$ is nothing, alkoxy, $OCH_2COOEt$ or halogen $R_2$ and $R_3$ are independently hydrogen, alkyl, alkoxy, hydroxy, or $OCH_2COOAlk$; and $R_4$ and $R_5$ are hydrogens or form together a saturated or unsaturated of 5-7 carbocyclic ring; or its isomer, salt, hydrate, N-oxide, crystal or any combination thereof; and a carrier, diluents, or any combination thereof

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention provides a compound represented by the structure represented by formula I:

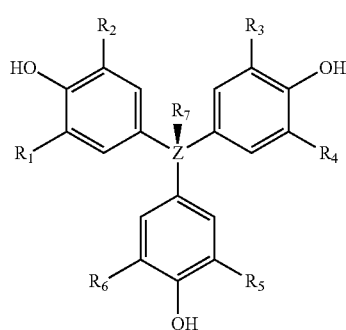

I wherein

Z is carbon, nitrogen, phosphor, arsenic, silicon or germanium;

$R_1$, $R_2$, $R_3$, $R_4$, $R_5$ and $R_6$ are independently the same or different comprising alkyl ($C_2$-$C_6$), alkenyl ($C_2$-$C_6$), alkynyl ($C_2$-$C_6$), alkoxy ($C_2$-$C_6$), alkylalkoxy, haloalkyl, alkylhaloalkyl, aryl, alkylaryl, haloaryl, cycloalkyl, heterocycloalkyl, alkylcycloalkyl, alkylheterocycloalkyl, heteroaryl, alkylheteroaryl, amino, monoalkylamino, dialkylamino or arylamino; and $R_7$ is nothing, oxo, hydrogen, hydroxy, halogen, CN, $NO_2$, alkyl ($C_1$-$C_6$), alkenyl ($C_1$-$C_6$), alkynyl ($C_1$-$C_6$), alkoxy ($C_1$-$C_6$), haloalkyl, aryl, alkylaryl, haloaryl, heterocycloalkyl, alkylheterocycloalkyl, heteroaryl or alkylheteroaryl; or its isomer, salt, hydrate, N-oxide, crystal or any combination thereof.

In another embodiment Z is carbon. In another embodiment $R_7$ is a methyl group. In another embodiment $R_1$, $R_2$, $R_3$, $R_4$, $R_5$, and $R_6$ are —$(CH_2)_n$-heterocycloalkyl group, wherein n is between 1-6. In another embodiment $R_1$, $R_2$, $R_3$, $R_4$, $R_5$, and $R_6$ are —$(CH_2)_n$-aminoalkyl group, wherein n is between 1-6. In another embodiment $R_1$, $R_2$, $R_3$, $R_4$ $R_5$, and $R_6$ are —$(CH_2)_n$-dialkylamino group, wherein n is between 1-6. In another embodiment $R_1$, $R_2$, $R_3$, $R_4$, $R_5$, and $R_6$ are —$(CH_2)n$-$N(CH_3)_2$ group, wherein n is between 1-6. In another embodiment $R_1$, $R_2$, $R_3$, $R_4$, $R_5$, and $R_6$ are —$(CH_2)_n$—$N(Et)_2$ group, wherein n is between 1-6. In another embodiment $R_1$, $R_2$, $R_3$, $R_4$, $R_5$, and $R_6$ are —$(CH_2)_n$-aryl group, wherein n is between 1-6. In another embodiment $R_1$, $R_2$, $R_3$, $R_4$ $R_5$, and $R_6$ are —$(CH_2)_n$-heteroaryl group, wherein n is between 1-6. In another embodiment $R_1$, $R_2$, $R_3$, $R_4$, $R_5$, and $R_6$ are —$(CH_2)_n$-haloalkyl group, wherein n is between 1-6. In another embodiment $R_1$, $R_2$, $R_3$, $R_4$, $R_5$, and $R_6$ are —$(CH_2)_n$-alkoxy group, wherein n is between 1-6. In another embodiment $R_1$, $R_2$, $R_3$, $R_4$, $R_5$, and $R_6$ are —$(CH_2)_n$-ethoxy group, wherein n is between 1-6. In another embodiment $R_1$, $R_2$, $R_3$, $R_4$, $R_5$, and $R_6$ are —$(CH_2)_n$-cycloalkyl group, wherein n is between 1-6.

In one embodiment, this invention provides a compound represented by the structure represented by formula II:

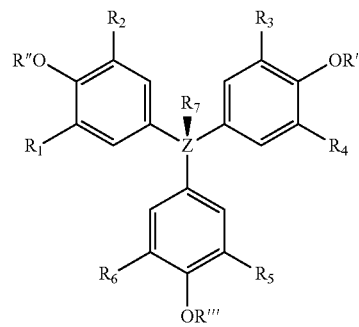

II wherein

Z is carbon, nitrogen, phosphor, arsenic, silicon or germanium;

R', R" and R'" are independently the same or different comprising hydrogen, alkyl, haloalkyl, alkylamino, alkylester, phenyl, benzyl, alkanyloyl, acetyl or benzoyl;

$R_1$, $R_2$, $R_3$, $R_4$, $R_5$ and $R_6$ are independently the same or different comprising alkyl ($C_2$-$C_6$), alkenyl ($C_2$-$C_6$), alkynyl ($C_2$-$C_6$), alkoxy ($C_2$-$C_6$), alkylalkoxy, haloalkyl, alkylhaloalkyl, aryl, alkylaryl, haloaryl, cycloalkyl, heterocycloalkyl, alkylcycloalkyl, alkylheterocycloalkyl, heteroaryl, alkylheteroaryl, amino, monoalkylamino, dialkylamino or arylamino; and $R_7$ is nothing, oxo, hydrogen, hydroxy, halogen, CN, $NO_2$, alkyl ($C_1$-$C_6$), alkenyl ($C_1$-$C_6$), alkynyl ($C_1$-$C_6$), alkoxy ($C_1$-$C_6$), haloalkyl, aryl, alkylaryl, haloaryl, heterocycloalkyl, alkylheterocycloalkyl, heteroaryl or alkylheteroaryl; or its isomer, salt, hydrate, N-oxide, crystal or any combination thereof.

In one embodiment, this invention provides a compound represented by the structure of formula III:

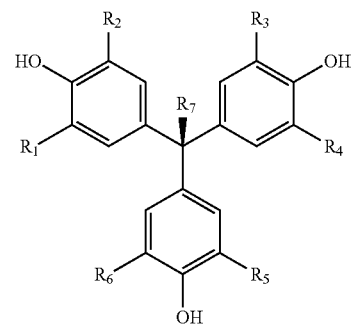

III wherein $R_1$, $R_2$, $R_3$, $R_4$, $R_5$, and $R_6$ areas defined above and $R_7$ is oxo, hydrogen, hydroxy, halogen, CN, $NO_2$, alkyl ($C_1$-$C_6$), alkenyl ($C_1$-$C_6$), alkynyl ($C_1$-$C_6$), alkoxy ($C_1$-$C_6$), haloalkyl, aryl, alkylaryl, haloaryl, heterocycloalkyl, alkylheterocycloalkyl, heteroaryl or alkylheteroaryl; or its isomer, salt, hydrate, N-oxide, crystal or any combination thereof.

In one embodiment, this invention provides a compound represented by the structure of formula IV:

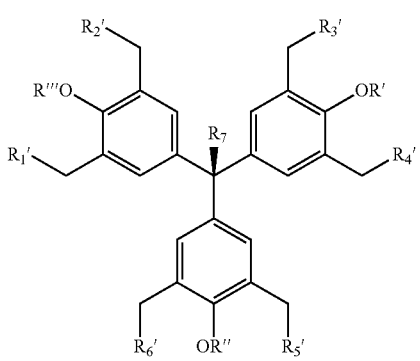

wherein

R', R'', R''' are independently the same or different comprising hydrogen, alkyl, haloalkyl, phenyl, alkylester, benzyl, alkanyloyl, acetyl or benzoyl;

$R_1'$, $R_2'$, $R_3'$, $R_4'$ $R_5'$, and $R_6'$ are the same or different comprising halogen, aryl, alkyl, cycloalkyl, heterocycloalkyl, alkoxy ($C_2$-$C_6$), amino, monoalkylamino, dialkylamino or arylamino group; and $R_7$ is oxo, hydrogen, hydroxy, halogen, CN, $NO_2$, alkyl ($C_1$-$C_6$), alkenyl ($C_1$-$C_6$), alkynyl ($C_1$-$C_6$), alkoxy ($C_1$-$C_6$), haloalkyl, aryl, alkylaryl, haloaryl, heterocycloalkyl, alkylheterocycloalkyl, heteroaryl or alkylheteroaryl; or its isomer, salt, hydrate, N-oxide, crystal or any combination thereof.

In another embodiment, $R_1'$, $R_2'$, $R_3'$, $R_4'$ $R_5'$, and $R_6'$ are dialkylamino group. In another embodiment, $R_1'$, $R_2'$, $R_3'$, $R_4'$ $R_5'$, and $R_6'$ are dimethylamino group. In another embodiment, $R_1'$, $R_2'$, $R_3'$, $R_4'$ $R_5'$, and $R_6'$ are diethylamino group. In another embodiment, $R_1'$, $R_2'$, $R_3'$, $R_4'$ $R_5'$, and $R_6'$ are N-piperidine group. In another embodiment, $R_1'$, $R_2'$, $R_3'$, $R_4'$ $R_5'$, and $R_6'$ are N-pyrolidine group. In another embodiment, $R_1'$, $R_2'$, $R_3'$, $R_4'$ $R_5'$, and $R_6'$ are N-piperazine group. In another embodiment, $R_1'$, $R_2'$, $R_3'$, $R_4'$ $R_5'$, and $R_6'$ are N-piperazine-4-methyl group. In another embodiment, $R_1'$, $R_2'$, $R_3'$, $R_4'$ $R_5'$, and $R_6'$ are N-morpholine group. In another embodiment, $R_1'$, $R_2'$, $R_3'$, $R_4'$ $R_5'$, and $R_6'$ are ethoxy group.

In one embodiment, this invention provides a compound represented by the structure of formula V:

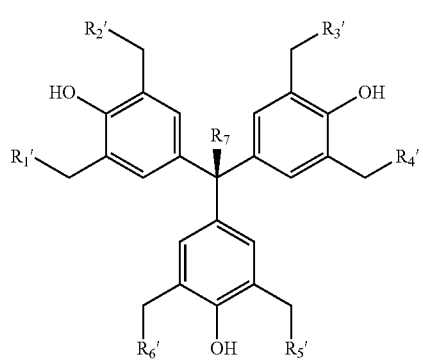

wherein $R_1'$, $R_2'$, $R_3'$, $R_3'$, $R_4'$ $R_5'$, and $R_6'$ are the same or different comprising halogen, aryl, alkyl, cycloalkyl, heterocycloalkyl, alkoxy ($C_2$-$C_6$), amino, monoalkylamino, dialkylamino or arylamino group; and $R_7$ is and $R_7$ is oxo, hydrogen, hydroxy, halogen, CN, $NO_2$, alkyl ($C_1$-$C_6$), alkenyl ($C_1$-$C_6$), alkynyl ($C_1$-$C_6$), alkoxy ($C_1$-$C_6$), haloalkyl, aryl, alkylaryl, haloaryl, heterocycloalkyl, alkylheterocycloalkyl, heteroaryl or alkylheteroaryl.

In another embodiment, $R_1'$, $R_2'$, $R_3'$, $R_4'$ $R_5'$, and $R_6'$ are dialkylamino group. In another embodiment, $R_1'$, $R_2'$, $R_3'$, $R_4'$ $R_5'$, and $R_6'$ are dimethylamino group. In another embodiment, $R_1'$, $R_2'$, $R_3'$, $R_4'$ $R_5'$, and $R_6'$ are diethylamino group. In another embodiment, $R_1'$, $R_2'$, $R_3'$, $R_4'$ $R_5'$, and $R_6'$ are N-piperidine group. In another embodiment, $R_1'$, $R_2'$, $R_3'$, $R_4'$ $R_5'$ and $R_6'$ are N-pyrolidine group. In another embodiment, $R_1'$, $R_2'$, $R_3'$, $R_4'$ $R_5'$, and $R_6'$ are N-piperazine group. In another embodiment, $R_1'$, $R_2'$, $R_3'$, $R_4'$ $R_5'$, and $R_6'$ are N-piperazine-4-methyl group. In another embodiment, $R_1'$, $R_2'$, $R_3'$, $R_4'$ $R_5'$, and $R_6'$ are N-morpholine group. In another embodiment, $R_1'$, $R_2'$, $R_3'$, $R_4'$ $R_5'$, and $R_6'$ are ethoxy group.

In one embodiment, this invention provides a compound represented by the structure of formula VI:

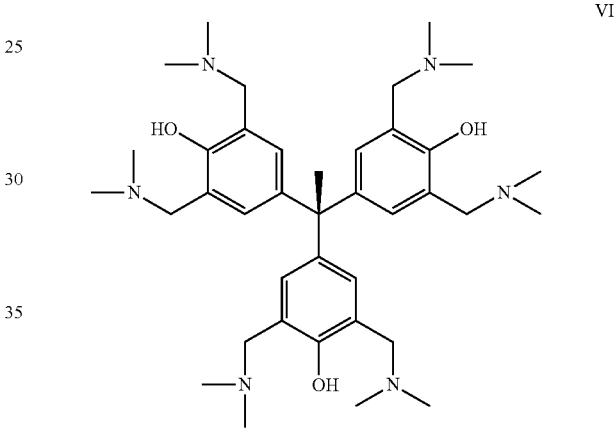

and its pharmaceutical composition comprising the same.

In one embodiment, this invention provides a compound represented by the structure of formula VII:

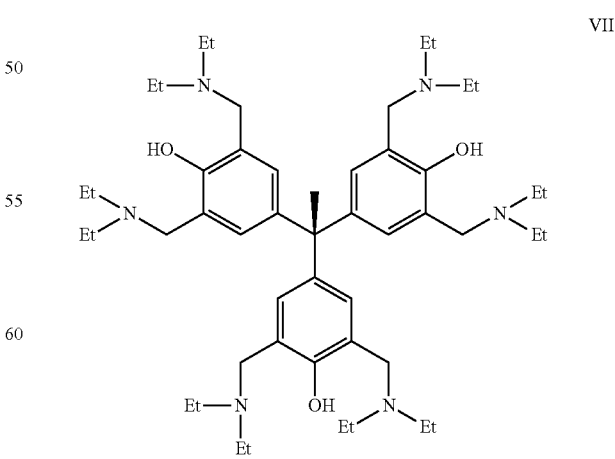

and its pharmaceutical composition comprising the same.

In one embodiment, this invention provides a compound represented by the structure of formula VIII:

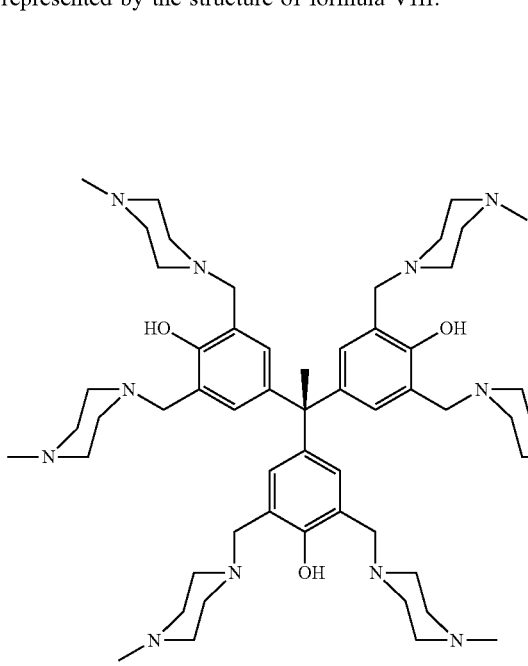

VIII and its pharmaceutical composition comprising the same.

In one embodiment, this invention provides a compound represented by the structure of formula IX:

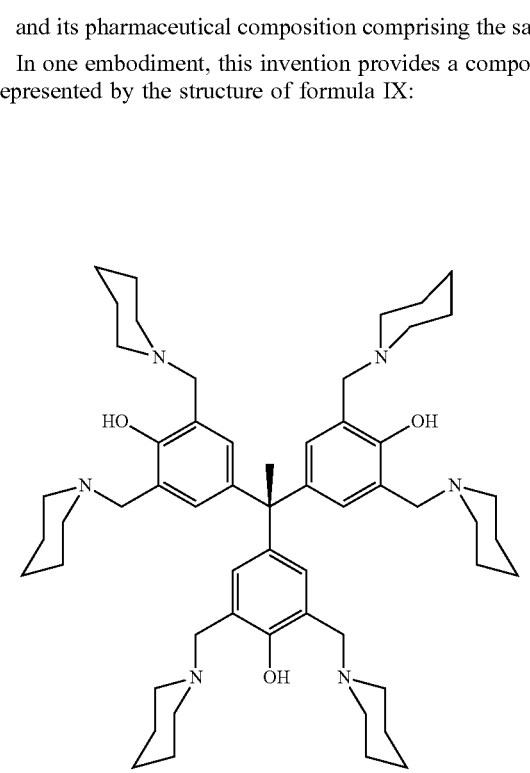

IX and its pharmaceutical composition comprising the same.

In one embodiment, this invention provides a compound represented by the structure of formula X:

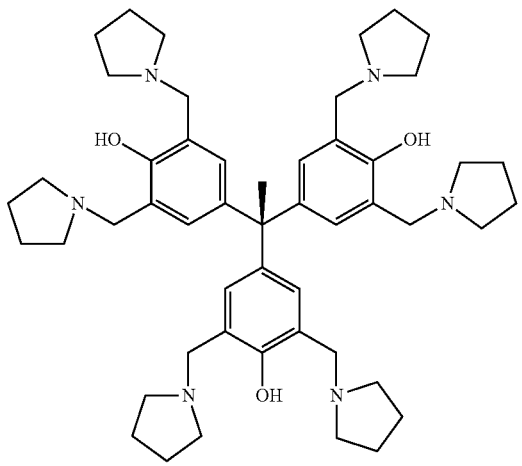

X and its pharmaceutical composition comprising the same.

In one embodiment, this invention provides a compound represented by the structure of Formula XI:

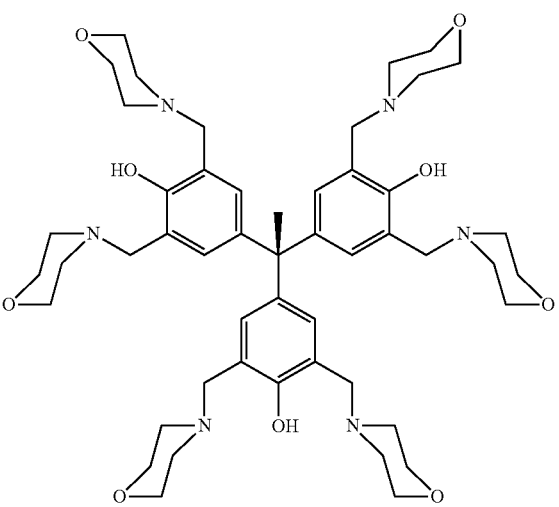

XI and its pharmaceutical composition comprising the same.

In one embodiment, this invention provides a compound represented by the structure represented by formula XII:

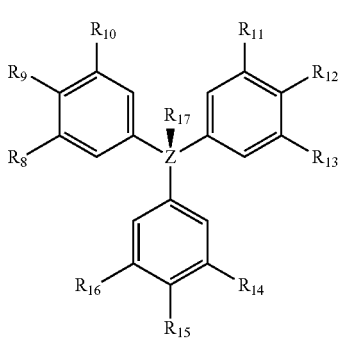

XII wherein

Z is carbon, nitrogen, phosphor, arsenic, silicon or germanium;

$R_8$ to $R_{16}$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl alkenyl, alkynyl, aryl, arylalkyl, alkylaryl, arylsulfonyl, arylalkylenesulfonyl, alkoxy, haloalkyl, haloaryl, aryloxy, amino, monoalkylamino, dialkylamino, alkylamido, arylamino, arylamido, alkylthio, arylthio, heterocycloalkyl, alkylheterocycloalkyl, heterocycloalkylalkyl, heteroaryl, heteroarylalkyl, alkylheteroaryl; or $R_{10}$, $R_{11}$, or $R_{14}$, forms a fused cycloalkyl, heterocycloalkyl, aromatic or heteroaromatic ring with the main aromatic ring; and $R_{17}$ is H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, heteroarylalkyl, alkylheteroaryl; or its isomer, salt, hydrate, N-oxide, crystal or any combination thereof; and its pharmaceutical composition comprising the same and a carrier, diluents, or any combination thereof In one embodiment, this invention provides a compound represented by the structure represented by formula XIII:

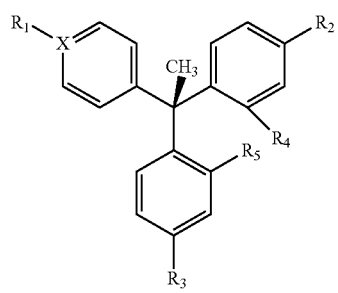

XIII wherein

X is carbon or nitrogen;

$R_1$ is nothing, alkoxy, $OCH_2COOEt$ or halogen $R_2$ and $R_3$ are independently hydrogen, alkyl, alkoxy, hydroxyl, or $OCH_2COOAlk$; and $R_4$ and $R_5$ are hydrogens or form together a saturated or unsaturated of 5-7 carbocyclic ring; or its isomer, salt, hydrate, N-oxide, crystal or any combination thereof; and its pharmaceutical composition comprising the same and a carrier, diluents, or any combination thereof.

In one embodiment, this invention provides a compound represented by the structure of formula XIV:

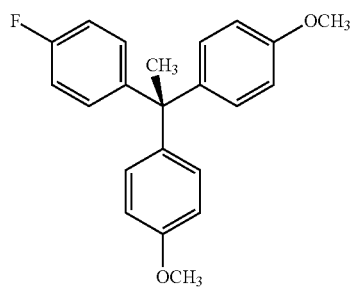

XIV and its pharmaceutical composition comprising the same and a carrier, diluents, or any combination thereof.

In one embodiment, this invention provides a compound represented by the structure of formula XV:

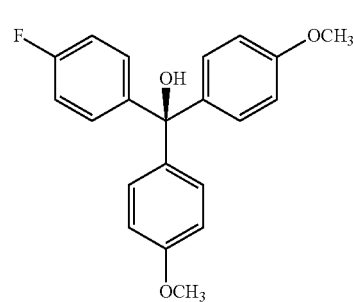

XV and its pharmaceutical composition comprising the same and a carrier, diluents, or any combination thereof.

In one embodiment, this invention provides a compound represented by the structure of formula XVI:

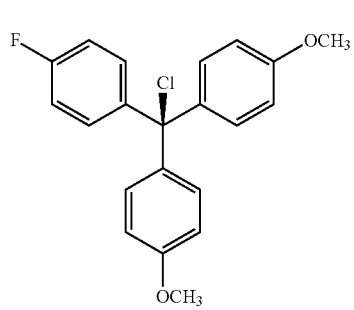

XVI and its pharmaceutical composition comprising the same and a carrier, diluents, or any combination thereof.

In one embodiment, this invention provides a compound represented by the structure of formula XVII:

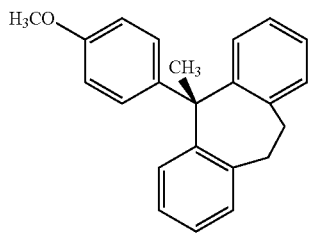

XVII and its pharmaceutical composition comprising the same; and
a carrier, diluents, or any combination thereof.

In one embodiment, this invention provides a compound represented by the structure of formula XVIII:

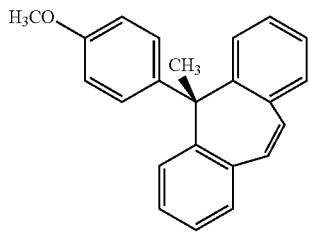

XVIII and its pharmaceutical composition comprising the same; and
a carrier, diluents, or any combination thereof.

In one embodiment, this invention provides a compound represented by the structure of formula XIX:

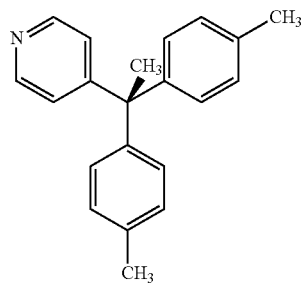

XIX and its pharmaceutical composition comprising the same; and
a carrier, diluents, or any combination thereof.

In one embodiment, this invention provides a compound is represented by the structure of formula XX:

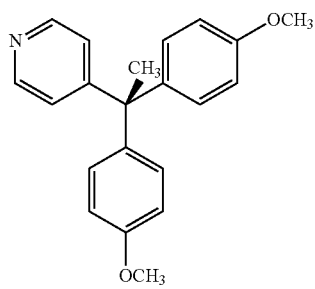

XX and its pharmaceutical composition comprising the same; and
a carrier, diluents, or any combination thereof.

In one embodiment, this invention provides a compound is represented by the structure of formula XXI:

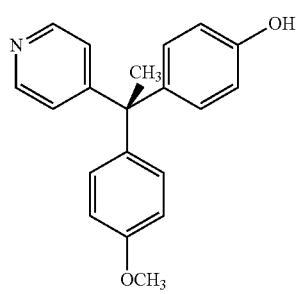

XXI and its pharmaceutical composition comprising the same; and
a carrier, diluents, or any combination thereof.

In one embodiment, this invention provides a compound is represented by the structure of formula XXII:

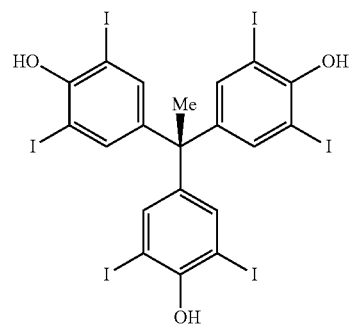

XXII and its pharmaceutical composition comprising the same; and
a carrier, diluents, or any combination thereof.

In one embodiment, this invention provides a compound represented by the structure of formula XXIII:

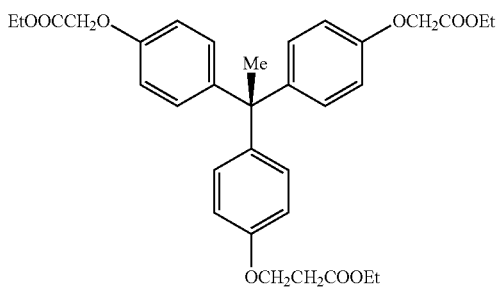

XXIII and its pharmaceutical composition comprising the same; and
a carrier, diluents, or any combination thereof.

In one embodiment, this invention provides a compound represented by the structure of Formula XXIV:

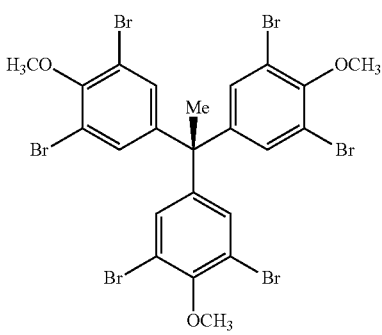

XXIV its pharmaceutical composition comprising the same; and a carrier, diluents, or any combination thereof.

In another embodiment, the fused heterocycloalkyl, with the main aromatic ring forms a phenylpyrrolidone group. In another embodiment, the fused aryl, with the main aromatic ring forms a naphtalene group. In another embodiment, the fused heteroaryl, with the main aromatic ring forms a quinoline or isoquinoline group.

In one embodiment, the heteroaryl is pyrrolyl, thienyl, thiazolyl, benzothienyl, naphthothienyl, purinyl isothiazolyl, furyl, furazanyl, isobenznzofuranyl, pyranyl, chromenyl, xanthenyl, phenoxyxanthiinyl, indolyl, isoindolyl, indolizinyl, isoindolyzinyl, benzothienyl, oxazolyl, isoxazolyl, pyrazolyl, pyridyl, pyrazinyl, pyrimidinyl, pyridazinyl, or any combination thereof.

In one embodiment said heterocycloalkyl is a cyclic urea, imidazolinyl, imidazolidinyl, pyrrolinyl, pyrrolidinyl, oxazolinyl, isoxazolinyl, oxazolidinyl, oxazolidonyl, isoxazolidonyl, pyrazolinyl, pyrazolidinyl, piperidyl, piperazine, morpholinyl.

The term "alkyl" refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-7 carbons. In another embodiment, the alkyl group has 2-6 carbons. In another embodiment, the alkyl group has 1-7 carbons. In another embodiment, the alkyl group has 2-8 carbons. In another embodiment, the alkyl group has 3-6 carbons. In another embodiment, the alkyl group has 3-7 carbons. In another embodiment, the alkyl group has 1-4 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or substituted by a halogen, haloalkyl, hydroxyl, alkoxy, carbonyl, amido, alkylamido, dialkylamido, nitro, cyano, amino, monoalkylamino, dialkylamino, carboxyl, thio and/or thioalkyl.

An "alkenyl" group refers, in one embodiment, to an unsaturated hydrocarbon, including straight chain, branched chain, and cyclic groups having one or more double bonds. The alkenyl group may have one double bond, two double bonds, three double bonds, etc. In another embodiment, the alkenyl group has 2-12 carbons. In another embodiment, the alkenyl group has 2-6 carbons. In another embodiment the alkenyl group has 2-4 carbons. In another embodiment the alkenyl group is ethenyl (—CH═CH$_2$) Examples of alkenyl groups are ethenyl, propenyl, butenyl, cyclohexenyl, etc. The alkenyl group may be unsubstituted or substituted by a halogen, hydroxy, alkoxy, carbonyl, amido, alkylamido, dialkylamido, nitro, cyano, amino, monoalkylamino, dialkylamino, carboxyl, thio and/or thioalkyl.

An alkynyl" group refers, in one embodiment, to an unsaturated hydrocarbon, including straight chain, branched chain and cyclic groups having one or more triple bonds. The alkynyl group may have one triple bond, two triple bonds, triple double bonds, etc. In another embodiment, the alkynyl group has 2-12 carbons. In another embodiment, the alkynyl group has 2-6 carbons. In another embodiment, the alkenyl group has 2-4 carbons. In another embodiment the alkynyl group is ethynyl (—CH═CH$_2$). Examples of alkynyl groups are ethynyl, propynyl, butynyl, cyclohexynyl, etc. The alkynyl group may be unsubstituted or substituted by a halogen, hydroxy, alkoxy, carbonyl, amido, alkylamido, dialkylamido, nitro, cyano, amino, monoalkylamino, dialkylamino, carboxyl, thio and/or thioalkyl.

An "alkoxy" group refers, in another embodiment is an alkyl group as defined above, which is linked to an oxygen. Examples of alkoxy groups are ethoxy, propoxy, tert-butoxy etc.

A "haloalkyl" group refers, in one embodiment, to an alkyl group as defined above, which is substituted by one or more halogen atoms, e.g. by F, Cl, Br or I.

An "aryl" group refers, in another embodiment, to an aromatic group having at least one carbocyclic aromatic group or heterocyclic aromatic group, which may be unsubstituted or substituted by one or more groups selected from halogen, haloalkyl, hydroxy, alkoxy, carbonyl, amido, alkylamido, dialkylamido, nitro, cyano, amino, monoalkylamino, dialkylamino, carboxy or thio or thioalkyl. In another embodiment, the aryl group is between 4-12 membered ring(s). In another embodiment, the aryl group is between 6-18 membered ring(s). In another embodiment, the aryl group is between 4-8 membered ring(s). In another embodiment, the aryl group is a 6 membered ring. In another embodiment, the aryl group is a fused ring system comprising of between 2-3 rings. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxy" group refers, in one embodiment, to an OH group. In some embodiments, when $R_1$, $R_2$ or $R_3$ of the compounds of the present invention is OR, then R is not OH.

In one embodiment, the term "halo" refers to a halogen, such as F, Cl, Br or I.

In another embodiment, the phrase "phenol" refers to an alcohol (OH) derivative of benzene.

An "amino" group refers to, in one embodiment, to a nitrogen atom attached by single bonds to hydrogen atoms, alkyl groups, alkenyl groups or aryl groups as described above, as described above, or a combination thereof. Non-limiting examples of amino groups are $NH_2$, $N(Me)_2$, $N(Et)_2$, $N(Ph)_2$ and the like.

A "cycloalkyl" group refers, in one embodiment, to a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, ($C_3$-$C_7$)cycloalkyl groups, such as cyclopropyl, cyclobutyl, cyclopentyl, cyclohexyl, and cycloheptyl, and saturated cyclic and bicyclic terpenes and ($C_3$-$C_7$)cycloalkenyl groups, such as cyclopropenyl, cyclobutenyl, cyclopentenyl, cyclohexenyl, and cycloheptenyl, and unsaturated cyclic and bicyclic terpenes. Preferably, the cycloalkyl group is a monocyclic ring or bicyclic to a ring structure comprising in addition to carbon atoms, sulfur, oxygen, nitrogen or any combination thereof, as part of the ring. In another embodiment the cycloalkyl is a 3-12 membered ring. In another embodiment the cycloalkyl is a 6 membered ring. In another embodiment the cycloalkyl is a 5-7 membered ring. In another embodiment the cycloalkyl is a 4-8 membered ring. In another embodiment, the cycloalkyl group may be unsubstituted or substituted by a halogen, haloalkyl, hydroxyl, alkoxy, carbonyl, amido, alkylamido, dialkylamido, cyano, nitro, $CO_2H$, amino, monoalkylamino, dialkylamino, carboxyl, thio and/or thioalkyl.

A "heterocycloalkyl" group refers, in one embodiment, to a non-aromatic, monocyclic or polycyclic ring comprising carbon and in addition to carbon, sulfur, phosphor, oxygen or nitrogen, as part of the ring. A heterocycloalkyl group can have one or more double bonds in the ring so long as the ring is not rendered aromatic by their presence. Examples of heterocycloalkyl groups include, but are not limited to, piperidine, piperazine, pyrane, morpholine. Preferably, the heterocycloalkyl group is a monocyclic ring or bicyclic to a ring structure comprising in addition to carbon atoms, sulfur, oxygen, nitrogen or any combination thereof, as part of the ring. In another embodiment the heterocycloalkyl is a 3-12 membered ring. In another embodiment the heterocycloalkyl is a 6 membered ring. In another embodiment the heterocycloalkyl is a 5-7 membered ring. In another embodiment the heterocycloalkyl is a 4-8 membered ring. In another embodiment, the heterocycloalkyl group may be unsubstituted or substituted by a halogen, haloalkyl, hydroxyl, alkoxy, carbonyl, amido, alkylamido, dialkylamido, cyano, nitro, $CO_2H$, amino, monoalkylamino, dialkylamino, carboxyl, thio and/or thioalkyl.

The terms "alkylalkoxy", "alkylhaloalkyl", "alkylaryl", "alkylcycloalkyl", "alkylheterocycloalkyl", "alkylheteroaryl" and "alkylamino" refer, in one embodiment, to an alkyl group, as defined above, linked to alkoxy, haloalkyl, aryl, cycloalkyl, heterocycloalkyl, heteroaryl or amino group, respectively. The alkoxy, haloalkyl, aryl, cycloalkyl, heterocycloalkyl, heteroaryl or amino groups are as defined hereinabove. Examples include, but are not limited to, $CH_2$—OEt, $CH_2$—N-piperidine, $CH_2$—N-piperazine, $CH_2$—N(Me)$_2$ etc.

Some embodiments of a synthetic procedure for some of the tri-aryl compounds are provided in scheme 1:

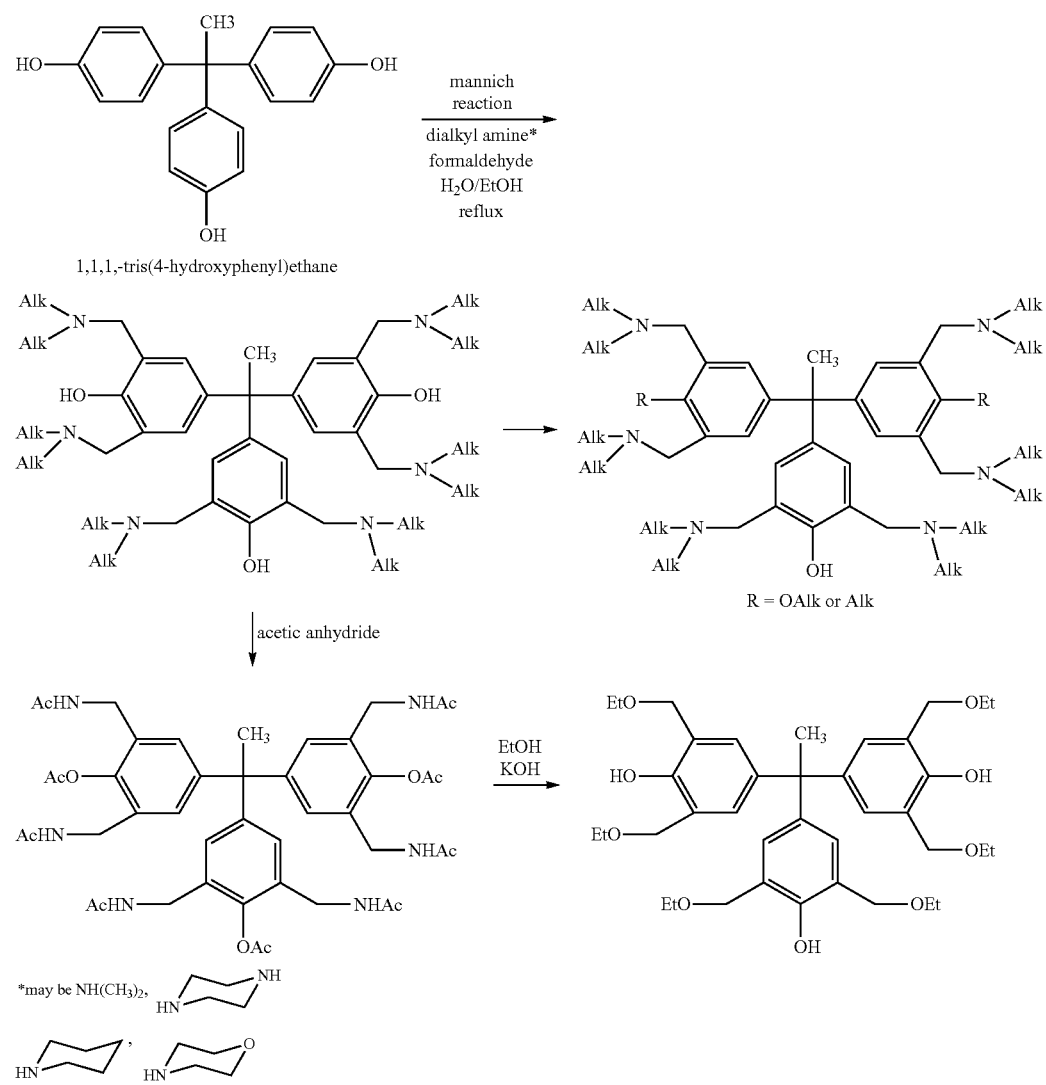

In another embodiment compounds IV-IX are prepared using the Mannich reaction as described in scheme 1 and in Example 1-7 using 1,1,1 tris(4-hydroxyphenyl)ethane as the starting material.

Some embodiments of a synthetic procedure for some of the tri-aryl compounds are provided in scheme 2:

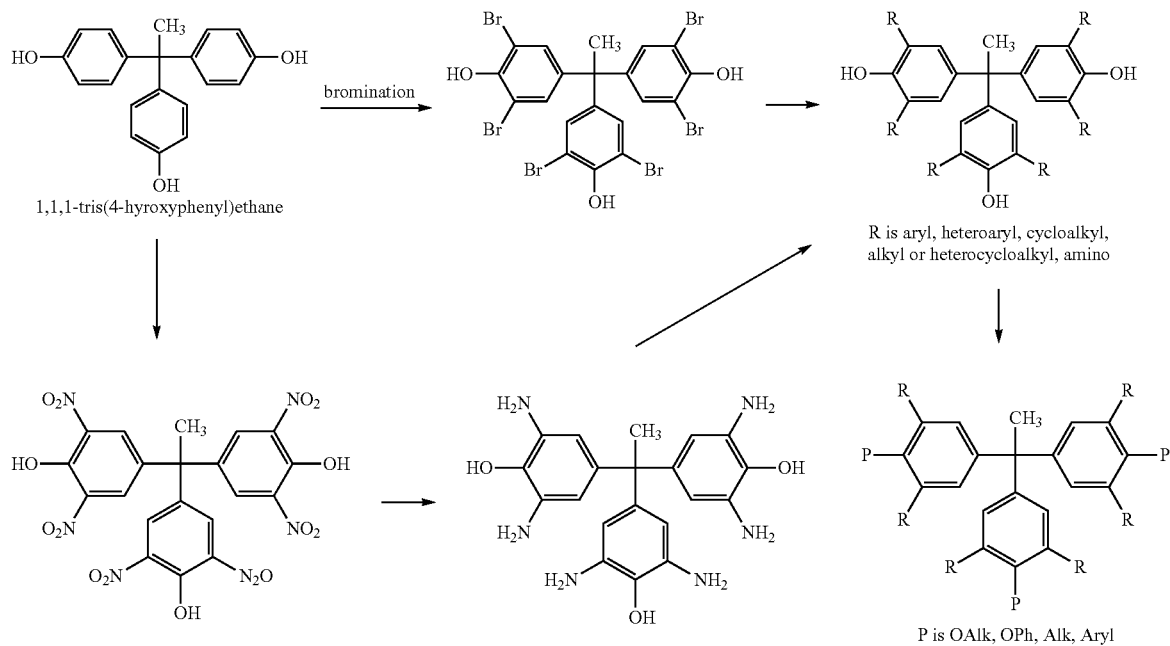

In another embodiment bromination or nitration of the commercial 1,1,1 tris(4-hydroxyphenyl)ethane provides the tris phenol substituted ortho positions. In another embodiment, exhaustive reaction conditions give the hexa substituted tris phenol. Methylation or alkylation lead to the tris-methoxy or tris-alkyl analogs.

Some embodiments of a synthetic procedure for some of the tri-aryl compounds are provided in scheme 3:

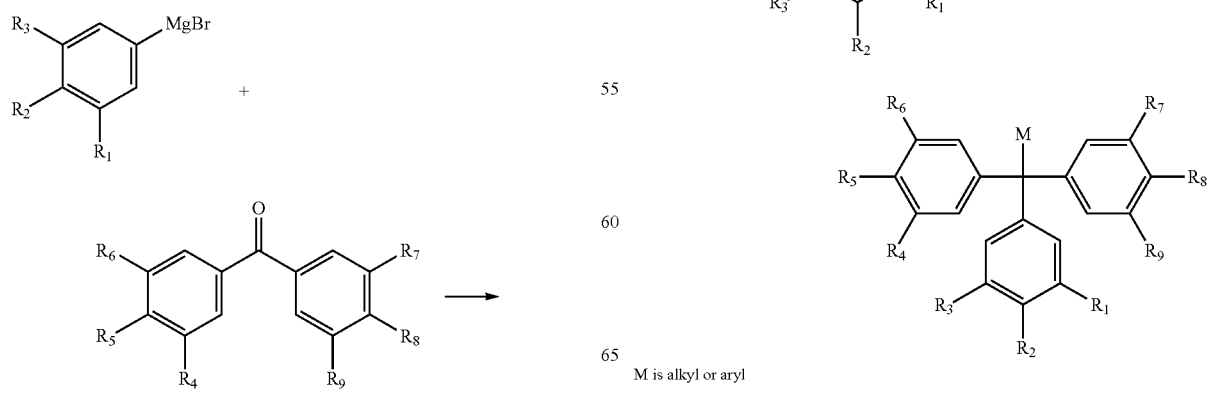

In one embodiment, a Grignard reaction of aryl magnesium bromide with aryl ester or diarylketone provides the triarylmethyl alcohol, as described in scheme 3. Chlorination of the triarylmethyl alcohol followed by its reaction with methylmagnesium iodide yields the compound as shown, with $R_{10}$ being a methyl group.

In one embodiment, this invention provides a pharmaceutical composition comprising the compounds of this invention and a carrier, diluent, or any combination thereof.

In one embodiment, this invention provides a pharmaceutical composition comprising a compound of formula I:

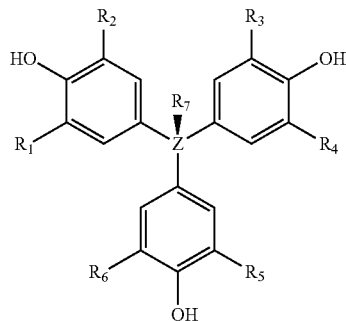

I wherein

Z is carbon, nitrogen, phosphor, arsenic, silicon or germanium;

$R_1$, $R_2$, $R_3$, $R_4$, $R_5$ and $R_6$ are independently the same or different comprising alkyl ($C_2$-$C_6$), alkenyl ($C_1$-$C_6$), alkynyl ($C_1$-$C_6$), alkoxy ($C_2$-$C_6$), alkylalkoxy, haloalkyl, alkylhaloalkyl, aryl, alkylaryl, haloaryl, cycloalkyl, heterocycloalkyl, alkylcycloalkyl, alkylheterocycloalkyl, heteroaryl, alkylheteroaryl, amino, monoalkylamino, dialkylamino, or arylamino; and $R_7$ is nothing, oxo, hydrogen, hydroxy, halogen, CN, $NO_2$, alkyl ($C_1$-$C_6$), alkenyl ($C_1$-$C_6$), alkynyl ($C_1$-$C_6$), alkoxy ($C_1$-$C_6$), haloalkyl, aryl, alkylaryl, haloaryl, heterocycloalkyl, alkylheterocycloalkyl, heteroaryl or alkylheteroaryl; and a carrier, diluents, or any combination thereof.

In another embodiment, the composition of formula I, further comprises an excipient, an additive or any combination thereof.

In one embodiment, this invention provides a pharmaceutical composition comprising a compound of formula II:

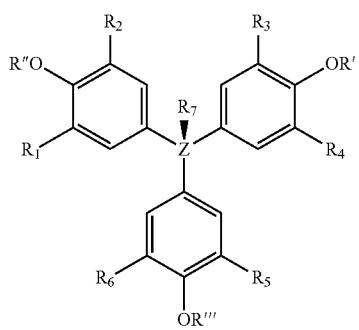

II wherein

Z is carbon, nitrogen, phosphor, arsenic, silicon or germanium;

R', and R'' R''' are independently the same or different comprising hydrogen, alkyl, haloalkyl, alkylamino, alkylester, phenyl, benzyl, alkanyloyl, acetyl or benzoyl;

$R_1$, $R_2$, $R_3$, $R_4$, $R_5$ and $R_6$ are independently the same or different comprising alkyl ($C_2$-$C_6$), alkenyl ($C_2$-$C_6$), alkynyl ($C_2$-$C_6$), alkoxy ($C_2$-$C_6$), alkylalkoxy, haloalkyl, alkylhaloalkyl, aryl, alkylaryl, haloaryl, cycloalkyl, heterocycloalkyl, alkylcycloalkyl, alkylheterocycloalkyl, heteroaryl, alkylheteroaryl, amino, monoalkylamino, dialkylamino, or arylamino; and $R_7$ is nothing, oxo, hydrogen, hydroxy, halogen, CN, $NO_2$, alkyl ($C_1$-$C_6$), alkenyl ($C_1$-$C_6$), alkynyl ($C_1$-$C_6$), alkoxy ($C_1$-$C_6$), haloalkyl, aryl, alkylaryl, haloaryl, heterocycloalkyl, alkylheterocycloalkyl, heteroaryl or alkylheteroaryl; and a carrier, diluents, or any combination thereof.

In another embodiment, the composition of formula II, further comprises an excipient, an additive or any combination thereof.

In some embodiments, this invention provides compositions which may comprise at least one compound of this invention, in any form or embodiment as described herein. In some embodiments, the term "a" is to be understood to encompass a single or multiple of the indicated material. In some embodiments, the term "a" or "an" refers to at least one.

In some embodiments, any of the compositions of this invention will consist of a compound of this invention, in any form or embodiment as described herein. In some embodiments, of the compositions of this invention will consist essentially of a compound of this invention, in any form or embodiment as described herein.

In some embodiments, the term "comprise" refers to the inclusion of the indicated active agent, such as the compounds of this invention, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient, or other active ingredients, however the primary compound mediating a therapeutic effect is the indicated active ingredient. In some embodiments, the term "consisting" refers to a composition, which contains the active ingredient and a pharmaceutically acceptable carrier or excipient.

In another embodiment, the invention provides a composition comprising a compound of this invention, as herein described, or its prodrug, analog, isomer, metabolite, derivative, pharmaceutically acceptable salt, pharmaceutical product, polymorph, crystal, impurity, N-oxide, ester, hydrate or any combination thereof and a suitable carrier or diluent.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The compositions of the present invention are formulated in one embodiment for oral delivery, wherein the active compounds may be incorporated with excipients and used in the form of ingestible tablets, buccal tables, troches, capsules, elixirs, suspensions, syrups, wafers, and the like. The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Syrup of elixir may contain the active compound, sucrose as a sweetening agent methyl, and propylparabens as preservatives, a dye and flavoring, such as cherry or orange flavor. In addition, the active compounds may be incorporated into sustained-release, pulsed release, controlled release or postponed release preparations and formulations.

In another embodiment, the compositions of this invention comprise one or more, pharmaceutically acceptable carrier materials.

In one embodiment, the carriers for use within such compositions are biocompatible, and in another embodiment, biodegradable. In other embodiments, the formulation may provide a relatively constant level of release of one active component. In other embodiments, however, a more rapid rate of release immediately upon administration may be desired. In other embodiments, release of active compounds may be event-triggered. The events triggering the release of the active compounds may be the same in one embodiment, or different in another embodiment. Events triggering the release of the active components may be exposure to moisture in one embodiment, lower pH in another embodiment, or temperature threshold in another embodiment. The formulation of such compositions is well within the level of ordinary skill in the art using known techniques. Illustrative carriers useful in this regard include microparticles of poly (lactide-co-glycolide), polyacrylate, latex, starch, cellulose, dextran and the like. Other illustrative postponed-release carriers include supramolecular biovectors, which comprise a non-liquid hydrophilic core (e.g., a cross-linked polysaccharide or oligosaccharide) and, optionally, an external layer comprising an amphiphilic compound, such as phospholipids. The amount of active compound contained in one embodiment, within a sustained release formulation depends upon the site of administration, the rate and expected duration of release and the nature of the condition to be treated suppressed or inhibited.

In one embodiment it will be desirable to deliver the compositions disclosed herein parenterally, intravenously, intramuscularly, or even intraperitoneally. Such approaches are well known to the skilled artisan, some of which are further described, for example, is U.S. Pat. No. 5,543,158; U.S. Pat. No. 5,641,515 and U.S. Pat. No. 5,399,363, all of which are fully incorporated by reference. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. It must be stable under the conditions of manufacture and storage and must be preserved against the contaminating action of microorganisms, such as bacteria and fungi.

In another embodiment, it will be preferable to include isotonic agents, for example, sugars or sodium chloride. In other embodiments, prolonged absorption of the injectable compositions will be desirable. Prolonged absorption of the injectable compositions can be brought about by the use of agents delaying absorption, for example, aluminum monostearate and gelatin, in the compositions.

Parenteral vehicles include in certain embodiments sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like In some embodiments, the compounds of this invention may be administered at various dosages to a subject, which in one embodiment, is a human subject. In one embodiment, the compounds of this invention is administered at a dosage of 0.1-200 mg per day. In one embodiment, the compound of this invention is administered at a dose of 0.1-10 mg, or in another embodiment, 0.1-25 mg, or in another embodiment, 0.1-50 mg, or in another embodiment, 0.3-15 mg, or in another embodiment, 0.3-30 mg, or in another embodiment, 0.5-25 mg, or in another embodiment, 0.5-50 mg, or in another embodiment, 0.75-15 mg, or in another embodiment, 0.75-60 mg, or in another embodiment, 1-5 mg, or in another embodiment, 1-20 mg, or in another embodiment, 3-15 mg, or in another embodiment, 1-30 mg, or in another embodiment, 30-50 mg, or in another embodiment, 30-75 mg, or in another embodiment, 100-2000 mg. In some embodiments, the compounds of this invention may be administered at different dosages, as a function of time, or disease/symptom/condition severity, or age, or other factors, as will be appreciated by one skilled in the art.

The compounds of this invention may be administered at various dosages. In one embodiment, the compounds of this invention are administered at a dosage of 1 mg. In another embodiment the compounds of this invention are administered at a dosage of 5 mg, or in another embodiment, 3 mg, or in another embodiment 10 mg, or in another embodiment 15 mg, or in another embodiment 20 mg, or in another embodiment 25 mg, or in another embodiment 30 mg, or in another embodiment 35 mg, or in another embodiment 40 mg, or in another embodiment 45 mg, or in another embodiment 50 mg, or in another embodiment 55 mg, or in another embodiment 60 mg, or in another embodiment 65 mg, or in another embodiment 70 mg, or in another embodiment 75 mg, or in another embodiment 80 mg, or in another embodiment 85 mg, or in another embodiment 90 mg, or in another embodiment 95 mg or in another embodiment 100 mg.

While the compounds of the invention can be administered as the sole active pharmaceutical agent, they can also be used in combination with one or more other compound, and/or in combination with other agents used in the treatment and/or prevention of the diseases, disorders and/or conditions, as will be understood by one skilled in the art. In another embodiment, the compounds of the present invention can be administered sequentially with one or more such agents to provide sustained therapeutic and prophylactic effects. In another embodiment, the compounds may be administered via different routes, at different times, or a combination thereof.

In addition, the compounds of the present invention can be used, either singly or in combination, in combination with other modalities for preventing or treating conditions, diseases or disorders. In some embodiments, such other treatment modalities may include without limitation, surgery, radiation, hormone supplementation, diet regulation, wound debridement, etc., as will be appropriate for the condition being treated. These can be performed sequentially (e.g., treatment with a compound of the invention following surgery or radiation) or in combination (e.g., in addition to a diet regimen).

The additional active agents may generally be employed in therapeutic amounts as indicated in the PHYSICIANS' DESK REFERENCE (PDR) 53rd Edition (1999), or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

The pharmaceutical composition can comprise the compounds of this invention alone or can further include a pharmaceutically acceptable carrier and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the compounds of this invention can be administered to a subject by, for example, subcutaneous implantation of a pellet; in a further embodiment, the pellet provides for controlled release of the compounds of this invention over a period of time. The preparation can also be administered by intravenous, intraarterial, or intramuscular injection of a liquid preparation, oral administration of a liquid or solid preparation, or by topical application. Administration can also be accomplished by use of a rectal suppository or a urethral suppository. The pharmaceutical composition can also be a parenteral formulation; is one embodiment, the formulation comprises a liposome that includes a complex of a compound of this invention.

The pharmaceutical composition of the invention can be prepared by known dissolving, mixing, granulating, or tablet-forming processes. For oral administration, the compounds of this invention or their physiologically tolerated derivatives such as salts, esters, N-oxides, and the like are mixed with additives customary for this purpose, such as vehicles, stabilizers, or inert diluents, and converted by customary methods into a suitable form for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders like acacia, cornstarch, gelatin, or with disintegrating agents such as cornstarch, potato starch, alginic acid, or with a lubricant such as stearic acid or magnesium stearate. Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the compounds of this invention or their physiologically tolerated derivatives such as salts, esters, N-oxides, and the like are converted into a solution, suspension, or emulsion, if desired with the substances customary and suitable for this purpose, for example, solubilizers or other auxiliaries. Examples are: sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, or pH buffering agents which enhance the effectiveness of the active ingredient.

For topical administration to body surfaces using, for example, creams, gels, drops, and the like, the compounds of this invention or their physiologically tolerated derivatives such as salts, esters, N-oxides, and the like are prepared and applied as solutions, suspensions, or emulsions in a physiologically acceptable diluent with or without a pharmaceutical carrier.

In another embodiment, the active compound can be delivered in a vesicle, in particular a liposome (see Langer, *Science* 249:1527-1533 (1990); Treat et al., in *Liposomes in the Therapy of Infectious Disease and Cancer*, Lopez-Berestein and Fidler (eds.), Liss, N.Y., pp. 353-365 (1989); Lopez-Berestein, ibid., pp. 317-327; see generally ibid).

In some embodiments, any of the compositions of this invention will comprise a compound of formula I-XXIV, in any form or embodiment as described herein. In some embodiments, any of the compositions of this invention will consist of a compound of formula I-XXIV, in any form or embodiment as described herein. In some embodiments, of the compositions of this invention will consist essentially of a compound of I-XXIV in any form or embodiment as described herein. In some embodiments, the term "comprise" refers to the inclusion of the indicated active agent, such as the compound of formula I-XXIV, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" refers to a composition, whose only active ingredient with a comparable mode of action, or comparable molecular target is the indicated active ingredient, however, other active ingredients may be incorporated, with such secondary active ingredients acting on different targets, or in a palliative capacity.

In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partner's i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

It is to be understood that this invention is directed to compositions and combined therapies as described herein, for any disease, disorder or condition, as appropriate, as will be appreciated by one skilled in the art. Certain applications of such compositions and combined therapies have been described hereinabove, for specific diseases, disorders and conditions, representing embodiments of this invention, and methods of treating such diseases, disorders and conditions in a subject by administering a compound as herein described, alone or as part of the combined therapy or using the compositions of this invention represent additional embodiments of this invention.

In some embodiments, the compounds of this invention modulates the activity of a nucleic acid polymerase. In some embodiments, the term "modulate" refers to the compound's enhancement or stimulation of enzyme activity. In some embodiments, according to this aspect of the invention, the compounds of this invention promote greater activity of a nucleic acid polymerase. In some embodiments, such promotion is direct, or in some embodiments, such promotion of enhanced activity is indirect.

Such effects on polymerase activity can be readily ascertained by standard methodology known in the art, for example, via performance of co-immunoprecipitation assays to ascertain binding of the compound to the polymerase, performance of quantitative PCR to determine effects of the compound on polymerase activity, and others. See for example, See, for example, "Molecular Cloning: A laboratory Manual" Sambrook et al., (1989); "Current Protocols in Molecular Biology" Volumes I-III, Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et. al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. L. ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterisation—A Laboratory Course Manual" CSHL Press (1996); all of which are incorporated fully by reference herein.

The following examples are presented in order to more fully illustrate the preferred embodiments of the invention. They should in no way be construed, however, as limiting the broad scope of the invention.

Example 1

Synthesis of Compound of Formula VI 1,1,1-tris(4-hydroxyphenyl)ethane (4 g, 13 mM), formaldehyde (3.6 g, 120 mM) and a 40% solution of dimethylamine in water (15 ml) were added to a solution of 50 ml water and 60 ml EtOH. The solution was refluxed for 2.5 hours. Partial evaporation of the solvent precipitated a white solid, which was filtered, washed with water and dried to give 7.85 g white solid of compound of formula VI, 93% yield, mp.=169°.
NMR $CDCl_3^{TM}$ 6.64 (6H, s, ArH), 3.40 (12H, s, $CH_2$), 2.22 (36H, s, N—$CH_3$), 2.06 (3H, s, C—$CH_3$).

Example 2

Synthesis of Compound of Formula VII

Compound of formula VII was synthesized by a process comparable to that described in Example 1.
NMR $CDCl_3^{TM}$ 6.71 (6H, s, ArH), 3.58 (12H, s, $CH_2$), 2.54 (24H, q, J=7.0 Hz), 1.04 (24H, t, J=7.0 Hz).

Example 3

Synthesis of Compound of Formula VIII 1,1,1-tris(4-hydroxyphenyl)ethane (1.53 gr, 5 mM), formaldehyde (1.35 gr, 45 mM) and 1-methyl piperazine (2.5 ml, 50 mM) in 20 ml water and 25 ml EtOH were refluxed for 3 hours. Evaporation provided a solid that by TLC and NMR contained 2 products, which was not the starting material. Formaldehyde (0.75 gr, 25 mM) and 1-methyl piperazine (1.5 ml, 30 mM) were added to 5 ml water and 10 ml EtOH and the reaction was refluxed for 4 hours. Evaporation and workup gave 3.3 gr light yellow-white solid, 67% yield, mp. –63°. Soluble in ethanol, and very good solubility in water.
NMR $CDCl_3^{TM}$ 6.67 (6H, s, ArH), 3.53 (12H, s, $CH_2$), 2.44 (48H, br.m, ring piperazine), 2.26 (18H, s, N—$CH_3$), 2.00 (3H, s, C—$CH_3$).

Example 4

Synthesis of Compound of Formula IX

A compound of formula IX was synthesized by a process comparable to that described in Example 1. A white solid was obtained. mp.=178°.

NMR CDCl$_3$$^{TM}$6.68 (6H, s, ArH), 3.55 (12H, s, CH$_2$), 2.51 (24H, br.t, N—CH$_2$ ring), 2.03 (3H, s, C—CH$_3$), 1.55 (24H, br.t, N—CH$_2$ ring), 1.42 (12H,br.s).

Example 5

Synthesis of Compound of Formula X

A compound of formula X was synthesized by a process comparable to that described in Example 1. A white solid was obtained. mp.=135°.

NMR CDCl$_3$$^{TM}$6.68 (6H, s, ArH), 3.61 (12H, s, CH$_2$), 2.51 (24H, br.t, N—CH$_2$ ring), 2.03 (3H, s, C—CH$_3$), 1.76 (24H, br.t, N—CH$_2$ ring).

Example 6

Synthesis of Compound of Formula XI

A compound of formula XI was synthesized by a process comparable to that described in Example 1. White solid was obtained. mp.=212°.

NMR CDCl$_3$$^{TM}$6.68 (6H, s, ArH), 3.69 (24H, t, J=4.5 Hz, N—CH$_2$ ring), 3.52 (12H, s, CH$_2$), 2.45 (24H, br.t, O—CH$_2$ ring), 2.03 (3H, s, C—CH$_3$).

Example 7

Synthesis of 1,1,1-tris(4-hydroxy-3,5-diethoxy-phenyl)-ethane

Step 1: Compound of formula IV (2.98 g, 4.6 mM), prepared by a process comparable to that described in Example 1 was added to 20 ml acetic anhydride, and heated to 100° for 4 hours. The mixture was cooled and water was added. The mixture was stirred overnight at room temperature, and then extracted with CH$_2$Cl$_2$. The solvent was evaporated to give a nona-acetate derivative as yellow oil and was farther purified by chromatography (silica gel; 1% MeOH/CH$_2$Cl$_2$) to give 3.2 gr of viscous yellow oil, 80% yield.

Step 2: A KOH (4 g) solution in water was added to a solution of the nona-acetate of step 1 (2.5 g) in 20 ml EtOH. The mixture was stirred for 20 hours at room temperature. The mixture was acidified with HCl, and extracted with CH$_2$Cl$_2$. The solvent was evaporated and gave 2.2 g of a yellow oil that and was further purified by column chromatography (silica gel; 2% MeOH/CH$_2$Cl$_2$) and recrystallized from toluene-hexane to give 1 gr of 1,1,1-tris(4-hydroxy-3,5-diethoxy-phenyl)-ethane, 53% yield, white solid, mp-78°. TLC–Rf=0.55 in 5% MeOH/CH$_2$Cl$_2$.

NMR CDCl$_3$$^{TM}$7.93 (3H, s, OH)), 6.79 (6H, s, Ar—H), 4.54 (12H, s, Ar—CH$_2$), 3.55 (12H, q, J=7.0 Hz, CH$_2$), 2.05 (3H, s, C—CH$_3$), 1.22 (18H, t, J=7.0 Hz, CH$_3$).

Example 8

Synthesis of 1,1,1-tris(4-hydroxy-3,5-dibromo-phenyl)-ethane

Step 1: A solution of NaOH (1 g, 25 mM) in 10 ml water and dimethyl sulphate (5.1 gr, 40 mM)(1:8 molar ratio) was added during 1 hour and simultaneously in portions to a solution of 1,1,1-tris(4-hydroxyphenyl)-ethane (1.53 g, 5 mM) in 20 ml ethanol and 10 ml water. The solution was then returned for 1 hour, and stirred 70 hours at RT. The white precipitate was filtered, washed with water and dried to give 1.74 g of 1,1,1-tris(4-methoxyphenyl)-ethane. Recrystallization twice from 50 ml ethanol gave 1.15 gr white crystals, 66% yield, m.p.-160°. TLC Rf=0.85 in CH$_2$Cl$_2$.

NMR CDCl$_3$$^{TM}$6.99, 6.79 (12H, AB$_q$, J$_{AB}$=8.8 Hz), 3.78 (9H, s, OCH$_3$), 2.11 (3H, s, CH$_3$).

Step 2: To a solution of 1,1,1-tris(4-methoxyphenyl)-ethane (0.49 gr, 1.4 mM,), from step 1, in 22 ml 1,2-dichloroethane, a solution of bromine (1.65 gr, 10.2) (7.3:1 ratio) in 5 ml 1,2-dichloroethane was added in portions. The solution was stirred at RT overnight and heated for 3 hours to 70°, and worked up (sodium thiosulphate) to give 1.0 gr crude product. TLC shows no starting material, but NMR showed mixtures, indicating that the bromination was not complete (m at 6.90 ppm, and 4 methoxy). The solid was brominated again with 1 gr bromine and refluxed 18 hours. The mixture was worked up as above and triturated with hot ethanol to give 0.27 gr white solid, 23% yield, mp=160°. TLC Rf=0.95 in CH$_2$Cl$_2$.

NMR CDCl$_3$$^{TM}$7.16 (6H, s, ArH), 3.92, 3.91 (6:4 ratio) (9H, 2s, OCH$_3$), 2.04, 2.03 (4:6 ratio)(3H, s, CH$_3$).

Example 9

Synthesis of 1,1,1-tris(4-hydroxy-3,5-diiodo-phenyl)-ethane (Compound XIV)

To 1,1,1-tris(4-hydroxyphenyl)-ethane (1.53 gr, 5 mM) in 40 ml ethanol and 40 ml water cooled in ice, see, KOH (2.2 gr, 39.2 mM) followed by KI (5.8 gr, 34.8 mM) and iodine (8.8 gr, 34.7 mM) were added. The color turns from violet to brown. The reaction was stirred at room temperature for 3 hours. The mixture was added to crushed ice. Concentrated HCl was added to obtain acidic pH and was treated with thiosulphate solution and extracted with dichloromethane. Evaporation gave 5.1 gr light brown solid, hexa iodo product followed by trituration in ethanol gave 3 gr white solid, 61% yield, mp=230°, RF=0.8 (in 5% MeOH—CH$_2$Cl$_2$).

NMR CDCl$_3$$^{TM}$7.3 (6H, s), 5.77 (br.s, OH), 1.97 (3H, s, CH$_3$).

While certain features of the invention have been illustrated and described, herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A compound represented by the structure of Formula XII, or its-salt, hydrate, or N-oxide thereof:

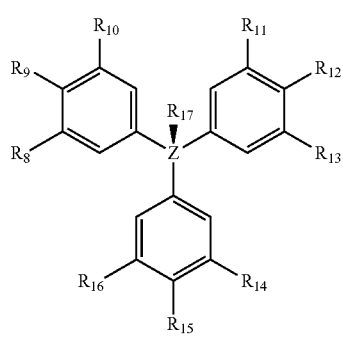

wherein
Z is carbon;
$R_8$, $R_{10}$, $R_{11}$, $R_{13}$, $R_{14}$, and $R_{16}$ are the same or different halogen,
$R_9$, $R_{12}$, and $R_{15}$ are the same or different $C_{1-6}$alkoxy; and
$R_{17}$ is $C_{1-6}$alkyl.
2. The compound of claim 1, wherein $R_{17}$ is $C_{1-4}$ alkyl.
3. The compound of claim 2, wherein $R_{17}$ is methyl.
4. The compound of claim 3, wherein the compound is:
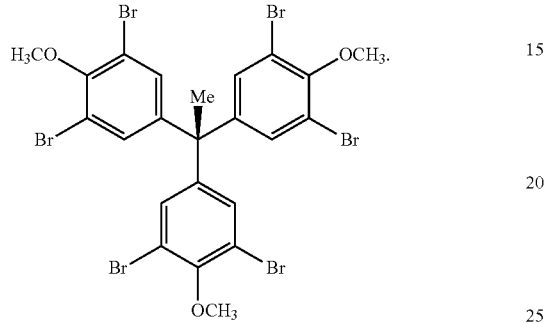
XXIV
* * * * *